United States Patent [19]

Schmidt et al.

[11] Patent Number: 4,614,723
[45] Date of Patent: Sep. 30, 1986

[54] PORPHYRIN DERIVATIVES AS FLUORESCENT MARKERS FOR IMMUNOASSAYS

[75] Inventors: Dieter Schmidt, Basel; Hans Steffen, Arisdorf, both of Switzerland

[73] Assignee: Hoffmann-La Roche Inc., Nutley, N.J.

[21] Appl. No.: 613,127

[22] Filed: May 23, 1984

[30] Foreign Application Priority Data

Jun. 3, 1983 [CH] Switzerland .................. 3045/83

[51] Int. Cl.[4] .......................... C07D 487/22
[52] U.S. Cl. .................. 436/536; 436/546; 436/800; 546/256; 540/145
[58] Field of Search .............. 436/536, 800, 546; 260/245.91; 546/256

[56] References Cited

U.S. PATENT DOCUMENTS

| | | | |
|---|---|---|---|
| 2,951,799 | 9/1960 | Sharp | 260/245.91 |
| 4,058,732 | 11/1977 | Wieder | 250/461.1 |
| 4,330,637 | 5/1982 | Wong | 260/245.91 |

FOREIGN PATENT DOCUMENTS

0071991  2/1983  European Pat. Off. .

OTHER PUBLICATIONS

Harriman, J. Chem. Soc., Faraday Transactions 2, (1981), 77, pp. 1695–1702.
Hendrickson, "Organic Chemistry", 3rd edition, McGraw Hill, (1970).
March, "Advanced Organic Chemistry", 2nd ed., McGraw Hill, (1977).

*Primary Examiner*—Robert J. Warden
*Assistant Examiner*—Robert Benson
*Attorney, Agent, or Firm*—Jon S. Saxe; George M. Gould; Patricia A. Coburn

[57] ABSTRACT

There are described novel porphyrin derivatives of the general formula

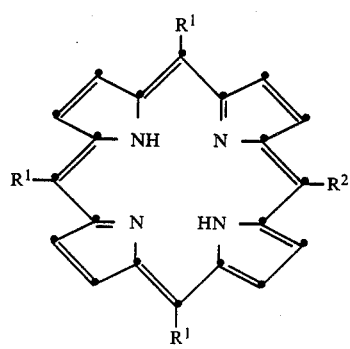

wherein either $R^1$ signifies the group

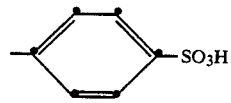

and $R^2$ signifies the group

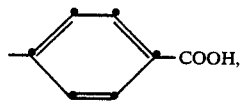 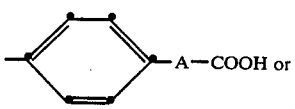

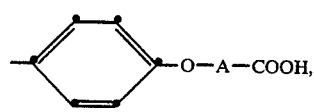

or $R^1$ signifies the group

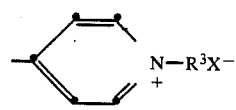

and $R^2$ signifies the group

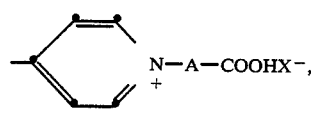

whereby $X^-$ signifies a halogen ion, an arylsulphonate ion, an alkylsulphonate ion or an alkyl sulphate ion, A signifies $(C_{1-8})$-alkylene and $R^3$ signifies $(C_{1-4})$-alkyl, and sulphonic acid salts of compounds of formula I in which $R^1$ signifies the group

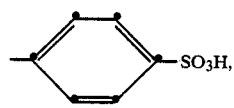

as well as a process for their manufacture and intermediates used in this process.

Because of their water-solubility the novel porphyrin derivatives are suitable as label molecules for highly sensitive fluorescence immuno-assays, especially for time-resolving fluorescence immuno-assays. The coupling of the novel porphyrin derivatives to immunologically-active materials is carried out in the customary manner, for example with a water-soluble carbodiimide derivative.

24 Claims, No Drawings

PORPHYRIN DERIVATIVES AS FLUORESCENT MARKERS FOR IMMUNOASSAYS

The present invention is concerned with porphyrin derivatives of the general formula

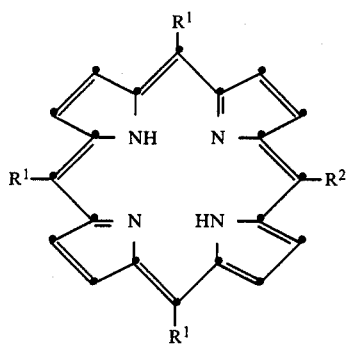

wherein either $R^1$ signifies the group

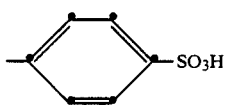

and $R^2$ signifies the group

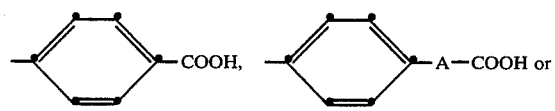

or $R^1$ signifies the group

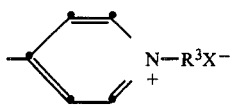

and $R^2$ signifies the group

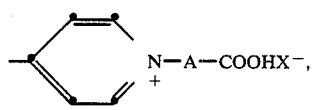

whereby $X^-$ signifies a halogen ion, an arylsulphonate ion, an alkylsulphonate ion or an alkyl sulphate ion, A signifies $(C_{1-8})$-alkylene and $R^3$ signifies $(C_{1-4})$alkyl, and sulfonic acid salts of compounds of formula I in which $R^1$ signifies the group

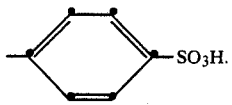

The present invention is also concerned with a process for the manufacture of these compounds and with intermediates used in this process.

The terms "alkyl" and "alkylene" denote straight-chain or branched-chain saturated hydrocarbon groups. The term "$(C_{1-4})$-alkyl" denotes groups containing 1 to 4 carbon atoms such as methyl and the like. The term "$(C_{1-8})$-alkylene" denotes groups containing 1 to 8 carbon atoms such as methylene, pentamethylene and the like. The term "halogen" taken alone or in combination such as in "halogen ion" denotes the halogens chlorine, bromine and iodine.

Preferred compounds of formula I in the scope of the present invention are:
4-[10,15,20-Tris(4-sulphophenyl)-21H,23H-porphin-5-yl]benzoic acid,
[4-[10,15,20-tris(4-sulphophenyl)-21H,23H-porphin-5-yl]phenoxy]acetic acid,
6-[4-[10,15,20-tris(4-sulphophenyl)-21H,23H-porphin-5-yl)phenyl]hexanecarboxylic acid,
1-(carboxymethyl)-1',1'',1'''-trimethyl-4,4',4'',4'''-(21H,23H-porphin-5,10,15,20-tetrayl)tetrakis-pyridinium tetraiodide,
1-(2-carboxyethyl)-1',1'',1'''-trimethyl-4,4',4'',4'''-(21H,23H-porphin-5,10,15,20-tetrayl)tetrakis-pyridinium bromide triiodide and
1-(5-carboxypentyl)-1',1'',1'''-trimethyl-4,4',4'',4'''-(21H,23H-porphin-5,10,15,20-tetrayl)tetrakis-pyridinium bromide triiodide.

The compounds of formula I and, when $R^1$ signifies the group

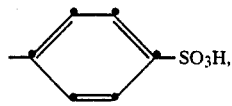

the corresponding sulphonic acid salts, can be manufactured in accordance with the invention by (a) reacting a compound of the general formula

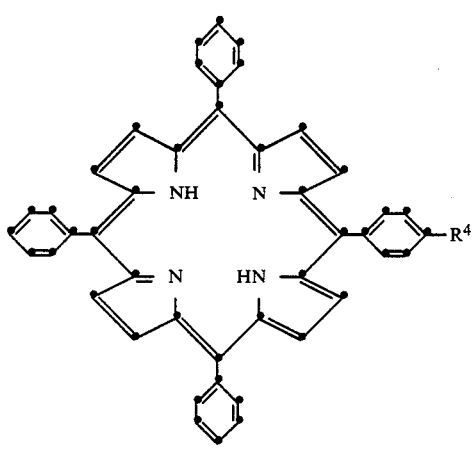

wherein R[4] signifies the group —COOH, —A—COOH or —O—A—COOH and A signifies (C$_{1-8}$)-alkylene, with an agent yielding the group —SO$_3$H, or (b) treating a compound of the general formula    5

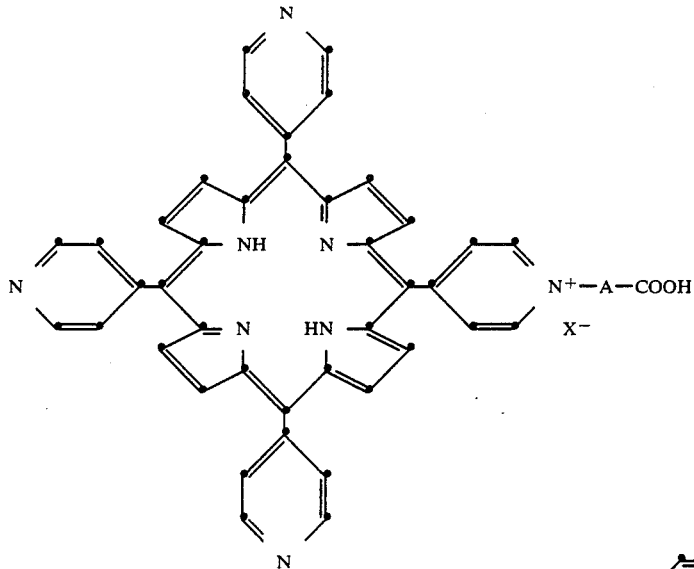

wherein A signifies (C$_{1-8}$)-alkylene and X⁻ signifies a halogen ion, an arylsulphonate ion, an alkylsulphonate ion or an alkyl sulphate ion, with an agent yielding a (C$_{1-4}$)-alkyl group and, if desired, (c) converting a compound obtained according to process (a) into a sulphonic acid salt.

In accordance with process variant (a) compounds of formula I in which R[1] signifies the group

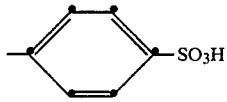

and R[2] signifies the group

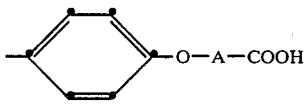

are manufactured by sulphonating the phenyl groups in a compound of formula II. Concentrated sulphuric acid is preferably used as the sulphonating agent and in this case the sulphonation is carried out at an elevated temperature (e.g. at about 100° C.). The desired sulphonation can, however, also be carried out according to other methods which are known per se.

In accordance with process variant (b) compounds of formula I in which R[1] signifies the group

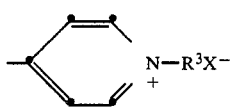

and R[2] signifies the group

III

N⁺—A—COOH
X⁻

are manufactured by alkylating the pyridine nitrogen atoms in a compound of formula III: As alkylating agents there can be used corresponding alkyl halides such as methyl iodide, arylsulphonic acid alkyl esters such as ethyl p-toluenesulphonate, alkylsulphonic acid alkyl esters, dialkyl sulphates such as diethyl sulphate, and the like. Suitable solvents are primarily polar solvents, for example alcohols such as methanol, and mixtures thereof with water. The reaction is preferably carried out at room temperature.

The manufacture of the sulphonic acid salts in accordance with process variant (c) is carried out according to methods which are known per se and which are familiar to any person skilled in the art. There come into consideration not only salts with inorganic bases (e.g. alkali metal salts) but also salts with organic bases (e.g. ammonium salts). The corresponding sodium salts are preferred.

The compounds of formula II used as starting materials are novel and are also an object of the present invention. They can be prepared by condensing pyrrole, benzaldehyde and an aldehyde of the general formula

IV

OHC—⟨ ⟩—R[4]

wherein R[4] has the above significance, with one another in the molar ratio 4:3:1. This condensation is carried out according to methods which are known per se and which are familar to any person skilled in the art. In a preferred embodiment, the pyrrole is placed in an acidic organic solvent such as acetic acid or propionic acid and a mixture of the two aldehydes (preferably in the molar ratio 3:1) is added slowly. The temperature is not critical, but the reaction is preferably carried out at an elevated temperature, for example at the boiling point of the reaction mixture. The separation of the product mixture is conveniently carried out in a manner known per se by chromatographic methods.

The compounds of formula IV are known or can be prepared according to methods known per se and in analogy to the preparation of known representatives of this class of substance.

The compounds of formula III used as starting materials are novel and are also an object of the present invention. They can be prepared by reacting the compound of the formula

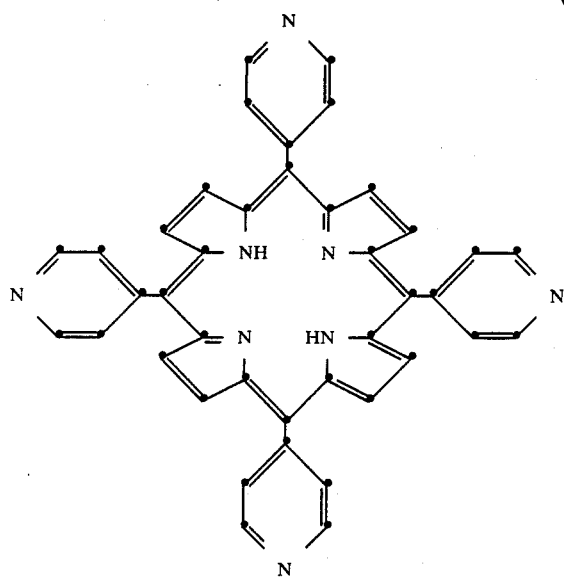

V with a compound of the general formula

X—A—COOH    VI wherein X and A have the above significance.

Suitable solvents are, for example, halogenated hydrocarbons such as methylene chloride and chloroform, alcohols such as methanol and ethanol, mixtures of the mentioned solvents and the like. Depending on the reactivity of the compound of formula VI used the reaction can be carried out in a temperature range of about room temperature up to the boiling point of the reaction mixture.

The compound of formula V can be prepared by condensing pyrrole with pyridine-4-carbaldehyde (molar ratio 1:1) according to methods which are adequately known. For example, the same reaction conditions as described earlier in connection with the preparation of compounds of formula II can be used.

The porphyrins of general formula I or their sulphonic acid salts can be detected very sensitively by fluorescence spectroscopy. Because they are water-soluble, they are best suited as label molecules for highly sensitive fluorescence immuno-assays. They are especially suitable for a time-resolving fluorescence immuno-assay as is described, for example, in U.S. Pat. No. 4,058,732. When the porphyrins of general formula I are used in place of the frequently used FITC (fluorescein isothiocyanate) the sensitivity of detection in fluorescence immuno-assays can be improved. This is especially advantageous in the determination of small amounts of antigens in body fluids such as, for example, plasma and serum. An example of such an antigen is carcinoembryonal antigen (CEA). The coupling of a compound of general formula I to an immunological material is carried out in the customary manner, for example with a water-soluble carbodiimide derivative such as 1-cyclohexyl-3-(2-morpholinoethyl)-carbodiimide p-toluenesulphonate.

The following Examples illustrate the present invention:

EXAMPLE 1

(a) A mixture of 2.5 ml of pyrrole and 134 ml of propionic acid is heated to boiling and then treated dropwise with a solution of 2 g of p-formylphenylcaproic acid and 3 ml of benzaldehyde in 5 ml of propionic acid. After heating to boiling under reflux for a further 30 minutes, the solution is left to cool to room temperature and the propionic acid is neutralized with a total of 9.5 g of sodium hydroxide (pH 4). The mixture is left to stand overnight and the black precipitate is then filtered off. The purification is carried out by column chromatography on 1.2 kg of silica gel, the elution being carried out with the following solvents in sequence: chloroform/cyclohexane (1:1), chloroform/ethyl acetate (3:2) and (2:3), ethyl acetate and ethyl acetate which contains 2% methanol. The thus-obtained product is chromatographed a further twice as described above and then recrystallized. For this purpose the product is dissolved in the smallest amount of chloroform possible, whereupon double the amount of methanol is added and the mixture is left to stand at 4° C. overnight. After filtration, the crystals are washed with methanol and then dried in vacuo at 20° C. There are obtained 810 mg (12%) of 6-[4-(10,15,20-triphenyl-21H,23H-porphin-5-yl)phenyl]hexanecarboxylic acid.

(b) 400 mg of finely powdered 6-[4-(10,15,20-triphenyl-21H,23H-porphin-5-yl)phenyl]hexanecarboxylic acid are suspended in 10 ml of concentrated sulphuric acid, this mixture is heated to 100° C. for 6 hours with the exclusion of moisture and light and then left to stand at 20° C. overnight. Subsequently, 15 ml of water are cautiously added thereto, whereby the mixture warms, and the mixture is again left to cool to room temperature. The precipitated green protonated product is filtered off, washed with a small amount of acetone, suspended in 15 ml of water together with some Celite and neutralized with saturated sodium bicarbonate solution until the solution changes in colour from green to red-violet. Residues of unreacted starting material are filtered off together with the Celite. The filtrate (about 100 ml) is dialyzed four times against 4 liters of water for 3 hours each time (in order to remove inorganic salts) and then lyophilized. The purification is carried out by chromatography on acrylamide gel AcA54 (LKB); elution agent: 150 mM sodium chloride solution which contains 10 mmol/l sodium phosphate (pH 7). The fractions containing pure product are pooled and dialyzed against water in order to remove the sodium chloride and then lyophilized. There are obtained 189 mg (35%) of 6-[4-[10,15,20-tris(4-sulphophenyl)-21H,23H-porphin-5-yl]phenyl]hexanecarboxylic acid tetrasodium salt.

UV: λ(ε), 414 (364000), 516 (12700), 553 (6100), 578 (5600), 634 (3400) nm.

EXAMPLE 2

(a) In analogy to the details in Example 1(a), from pyrrole, benzaldehyde and p-formylphenoxyacetic acid there is obtained [4-(10,15,20-triphenyl-21H,23H-porphin-5-yl)-phenoxy]acetic acid in a yield of 7%.

The p-formylphenoxyacetic acid used as the starting material is prepared from p-hydroxybenzaldehyde and iodoacetic acid in a manner known per se.

(b) In analogy to the details in Example 1(b), from [4-(10,15,20-triphenyl-21H,23H-porphin-5-yl)phenoxy]acetic acid there is obtained [4-[10,15,20-tris(4-sulphophenyl)-21H,23H-porphin-5-yl]phenoxy]acetic acid in a yield of 15%.

UV: $\lambda(\epsilon)$, 414 (397000), 517 (13000), 554 (6400), 579 (5600), 635 (3100) nm.

EXAMPLE 3

(a) 187 ml of propionic acid are heated at reflux while stirring and then treated firstly with 3.47 ml of pyrrole and then dropwise (within 15 minutes) with 4.81 ml of pyridine-4-carbaldehyde. After heating at reflux for 30 minutes, the solution is left to cool to room temperature, treated with 105 g of sodium hydroxide in 400 ml of water while cooling with ice and the black precipitate obtained is filtered off under suction. For purification, this precipitate is dissolved in 400 ml of chloroform and the product is then precipitated by the slow addition of 700 ml of cyclohexane. By three-fold suspension in a small amount of chloroform and subsequent suction filtration further impurities are removed. The further purification is carried out by two-fold column chromatography on silica gel; elution agent: chloroform, chloroform/methanol (9:1), chloroform/methanol (8:2) and chloroform/methanol (7:3). The material obtained is suspended in acetone, filtered off under suction and chromatographed on silica gel while eluting with chloroform which contains 3% methanol. There are obtained 600 mg (8%) of 5,10,15,20-tetra(4-pyridyl)-21H,23H-porphine.

(b) 180 mg of 5,10,15,20-tetra(4-pyridyl)-21H,23H-porphine are dissolved in 70 ml of chloroform/methanol (9:1), treated with 585 mg of 6-bromo-caproic acid and subsequently heated at reflux for 20 hours. The solution is then concentrated in vacuo to 5 to 10 ml and the product is precipitated by the addition of 250 ml of ether. The product is added to a 15 cm long silica column, whereupon the elution is carried out with 500 ml of chloroform/methanol (9:1), the starting zone is removed from the column and extracted with 1 liter of methanol and then with 1 liter of chloroform/methanol/water (2:7:1). The material obtained from the extracts is purified further by preparative thick-layer chromatography; eluent: chloroform/methanol/dimethylformamide/water (1:2:1:1). After scratching off, the main zone is extracted twice with 250 ml of methanol each time and twice with 250 ml of chloroform/methanol/water (2:7:1) each time. The product is finally re-precipitated a further four times. For this purpose, it is firstly dissolved in the smallest amount of methanol possible and then precipitated by the slow dropwise addition of 250 ml of chloroform. There are obtained 30 mg of 1-(5-carboxypentyl)-4-(10,15,20-tri-4-pyridyl-21H,23H-porphin-5-yl)pyridinium bromide.

(c) 20 mg of 1-(5-carboxypentyl)-4-(10,15,20-tri-4-pyridyl-21H,23H-porphin-5-yl)pyridinium bromide are dissolved in 50 ml of methanol/water (9:1), 3.5 g of methyl iodide are added thereto and the mixture is left to stand in the dark at room temperature for 6 days. Then, the solvent and the excess methyl iodide are removed in vacuo and the product is purified by re-precipitation. For this purpose, it is dissolved in the smallest amount of methanol possible (about 5 ml) and again precipitated by the slow dropwise addition of 250 ml of chloroform. This purification procedure is carried out three times in total. There are obtained 7 mg of 1-(5-carboxypentyl)-1',1'',1'''-trimethyl-4,4',4'',4'''-(21H,23H-porphin-5,10,15,20-tetrayl)tetrakispyridinium bromide triiodide.

UV: $\lambda(\epsilon)$, 422 (224000), 519 (14300), 556 (6200), 584 (6800), 640 (2000) nm.

EXAMPLE 4

(a) 15.2 ml of benzaldehyde and 7.51 g of 4-carboxybenzaldehyde are dissolved in 746 ml of boiling propionic acid, treated dropwise with 13.9 ml of pyrrole, the mixture obtained is subsequently heated under reflux for about 30 minutes and then left to cool to room temperature. The porphine derivative is precipitated by the addition of 0.5 l of water. The filtered-off crude product is pre-purified by two-fold column chromatography on 1.2 kg of silica gel, in each case the elution being carried out with the following solvents in sequence: chloroform/cyclohexane (1:1), chloroform/ethyl acetate (3:2) and (1:1), ethyl acetate and ethyl acetate which contains 2% methanol. For the further purification, the product is suspended in a small amount of methanol and filtered off. This procedure is repeated until the filtrate is only faintly coloured. The thus-obtained product is then chromatographed on a silica gel column using chloroform, chloroform/ethyl acetate (1:1) and ethyl acetate as the elution agent. There are obtained 1.7 g of 4-(10,15,20-triphenyl-21H,23H-porphin-5-yl)benzoic acid as violet crystals.

(b) In analogy to the details in Example 1(b), from 200 mg of 4-(10,15,20-triphenyl-21H,23H-porphin-5-yl)benzoic acid there are obtained 90 mg (33%) of pure 4-[10,15,20-tris(4-sulphophenyl)-21H,23H-porphin-5-yl]benzoic acid tetrasodium salt.

UV: $\lambda(\epsilon)$, 413 (418000), 517 (13600), 554 (6900), 578 (5900), 634 (3200) nm.

EXAMPLE 5

(a) 430 mg of tetrapyridylporphine are dissolved in 150 ml of chloroform/methanol (9:1), treated with 1.05 g of 3-bromo-propionic acid and the mixture is heated to 60° C. while stirring for 18 hours. The solution is then concentrated in vacuo to about 10 ml and the product is precipitated by the slow addition of 300 ml of ether. The filtered-off porphine mixture is added to a silica gel column (length 15 cm, diameter 2 cm), whereupon the elution is carried out using 500 ml of chloroform/methanol (9:1). The desired product remains behind as a violet zone at the start. This starting zone is removed from the column and extracted with 2 l of methanol and with 2 l of chloroform/methanol/dimethylformamide/water (1:2:1:1). The further purification of the product is carried out by preparative thick-layer chromatography [eluent: chloroform/methanol/dimethylformamide/water (1:2:1:1)]. After scratching off, the main zone is extracted four times with 250 ml of chloroform/methanol/water (2:7:1) each time. The product is finally re-precipitated a further four times by dissolving it in the smallest amount of chloroform/methanol/water (2:7:1) possible (about 40 ml) and then again precipitating by the slow dropwise addition of 300 ml of chloroform. There are obtained 42 mg of pure 1-(2-carboxyethyl)-4-(10,15,20-tri-4-pyridyl-21H,23H-porphin-5-yl)-pyridinium bromide as violet crystals.

(b) 40 mg of 1-(2-carboxyethyl)-4-(10,15,20-tri-4-pyridyl-21H,23H-porphin-5-yl)-pyridinium bromide are dissolved in 120 ml of chloroform/methanol/water (2:7:1), 7.1 g of methyl iodide are added thereto and the mixture is left to stand in the dark at room temperature for 6 days. The solution is then concentrated in vacuo to a volume of 20 ml and the product is precipitated by the slow addition of 20 ml of ether. The product is filtered off, washed with ether and purified by three-fold re-precipitation. For this purpose, it is dissolved each time in 20 ml of methanol and again precipitated by the slow dropwise addition of 200 ml of ether. There are obtained 18.5 mg of pure 1-(2-carboxyethyl)-1',1'',1'''-trimethyl-4,4',4'',4'''-(21H,23H-porphin-5,10,15,20-tetrayl)tetrakispyridinium bromide tri-iodide as a violet powder.

UV: $\lambda(\epsilon)$, 422 (236000), 519 (14600), 554 (5700), 584 (6200), 640 (1400) nm.

EXAMPLE 6

(a) 619 mg of tetrapyridylporphine and 2.79 g of iodoacetic acid are dissolved in 300 ml of chloroform/methanol (9:1) and this mixture is left to stand in the dark at room temperature for 22 hours. The solution is then concentrated to about 20 ml in vacuo and the product is precipitated by the slow dropwise addition of 400 ml of ether. The porphine mixture, which is filtered off and washed well with ether, is added to a silica gel column (length 15 cm, diameter 2 cm), whereupon the elution is carried out with 500 ml of chloroform/methanol (9:1). The desired product remains behind as a violet starting zone. This is removed from the column and extracted with chloroform/methanol/water (1:3.5:0.5). The further purification is carried out by preparative thick-layer chromatography (see Example 5) as well as by chromatography on a silica gel column [length 20 cm, diameter 1 cm, eluent: chloroform/methanol/water (2:7:1)]. The product is finally re-precipitated a total of three times by dissolving it in about 30 ml of chloroform/methanol/water (2:7:1) and then again precipitating by the slow dropwise addition of 300 ml of ether. There are obtained 68 mg of 1-(carboxymethyl)-4-(10,15,20-tri-4-pyridyl-21H,23H-porphin-5-yl)pyridinium iodide as a violet powder.

(b) 68 mg of 1-(carboxymethyl)-4-(10,15,20-tri-4-pyridyl-21H,23H-porphin-5-yl)pyridinium iodide are dissolved in 350 ml of chloroform/methanol/water (2:7:1), 14 g of methyl iodide are added thereto and the mixture is left to stand in the dark at room temperature for 6 days. The mixture is then concentrated to about 40 ml in vacuo, treated with 40 ml of methanol and the product is precipitated by the slow addition of 350 ml of ether. The product is filtered off, washed with ether and purified by three-fold re-precipitation. For this purpose, the product is in each case dissolved in 40 ml of methanol and again precipitated by the slow dropwise addition of 300 ml of ether. There are obtained 36 mg of 1-(carboxymethyl)-1',1'',1'''-trimethyl-4,4',4'',4'''-(21H,23H-porphin-5,10,15,20-tetrayl)tetrakispyridinium tetraiodide.

UV: $\lambda(\epsilon)$, 422 (210000), 519 (14100), 554 (6000), 584 (6200), 640 (1600) nm.

EXAMPLE 7

Labelling of anti-CEA with 6-[4-[10,15,20-tris(4-sulphophenyl)-21H,23H-porphin-5-yl]phenyl]hexanecarboxylic acid tetrasodium salt.

The coupling of the above-mentioned porphyrin derivative with anti-CEA was carried out as described below with the aid of the water-soluble carbodiimide derivative 1-cyclohexyl-3-(2-morpholinoethyl)-carbodiimide methyl-p-toluenesulphonate.

The following stock solutions are prepared for the coupling reaction:

1. 4 mg/ml of porphyrin derivative in water at pH 4.5; olive-green solution.
2. 2.9 mg/ml of anti-CEA from rabbits (DAKO Code No. A 115, Lot 042 A) in 200 mM NaHCO$_3$; pH 8.6.

400 µl of the stock solution 1 containing the porphyrin derivative are added to 3.2 mg of 1-cyclohexyl-3-(2-morpholinoethyl)-carbodiimide methyl-p-toluenesulphonate and intermixed briefly in a vortex. After 2 minutes, 400 µl of the anti-CEA stock solution 2 are added thereto and intermixed briefly in a vortex. The solution thereby becomes red in colour and has a pH of 8.2. This is adjusted to 8.6 with a small amount of 1N NaOH. The mixture is then left to stand in the dark at room temperature for 16 hours.

In order to separate the labelled anti-CEA, 500 µl of the mixture were chromatographed over a column (length 30 cm, diameter 9 mm) with acrylamide gel (AcA-54 from LKB) (elution agent: 150 mM sodium chloride, 10 mM sodium phosphate, 0.02% sodium azide, pH 7.0). The fractions containing the highest content of labelled anti-CEA were pooled (a total of 5 ml). In this solution there was determined by UV spectroscopy the content of anti-CEA (at 278 nm) and of porphyrin derivative (at 417 nm). The following concentrations were obtained:

$0.31 \times 10^{-6}$ M/l porphyrin derivative
and $0.73 \times 10^{-6}$ M/l anti-CEA.

This corresponds to a degree of labelling of 0.42.

EXAMPLE 8

Performance of a fluorescence immunoassay.

Quantitative determination of CEA standards with a monoclonal CEA antibody and a customary CEA antibody (rabbit):

Into the requisite number of test tubes (10×75 mm) there is in each case pipetted 0.250 ml of CEA standard solution (0 ng/ml CEA; 2.0 ng/ml/CEA; 5 ng/ml CEA; 10 ng/ml CEA and 20 ng/ml CEA in 0.2M/l sodium acetate, pH 5 with 4 g/l bovine serum albumin), in each case there is added a polystyrene bead (diameter 6.5 mm) sensitized with monoclonal mouse anti-CEA and incubation is then carried out at 37° C. for 24 hours.

The polystyrene beads are subsequently washed three times with 2 to 5 ml of distilled water each time and then transferred into test tubes each of which contains 0.250 ml of buffer solution with $2 \times 10^{10}$ M/l rabbit anti-CEA which is labelled with porphyrin derivative (degree of labelling 0.42). After incubation for 24 hours at 37° C., the beads are again washed three times with 2 to 5 ml of distilled water each time and transferred into test tubes each containing 2 ml of sulphuric acid (0.09N). After 30 minutes, the sulphuric acid solution is pipetted into measuring cuvettes and the content of porphyrin derivative (or anti-CEA) is measured by fluorescence spectroscopy (excitation wavelength 433 nm; emission wavelength 670 nm).

In Table I there are summarized the values of a CEA determination obtained with a series of CEA standards of ROCHE.

TABLE I

Fluorescence spectroscopic determination of CEA standards

| Concentration of CEA (ROCHE standard solutions) | Relative fluorescence intensity |
| --- | --- |
| 0 ng/ml CEA | 0.275 |
| 2 ng/ml CEA | 0.750 |
| 5 ng/ml CEA | 1.325 |
| 10 ng/ml CEA | 2.400 |
| 20 ng/ml CEA | 3.400 |

EXAMPLE 9

A normal human serum sample was analyzed using the same procedure as described in Example 8, whereby a CEA content of 1 ng/ml was found.

We claim:

1. A porphyrin compound of the formula:

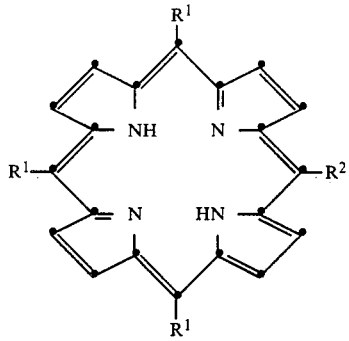

wherein $R^1$ is

$R^2$ is

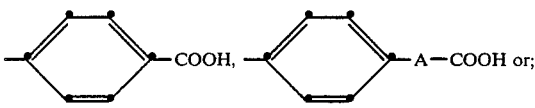

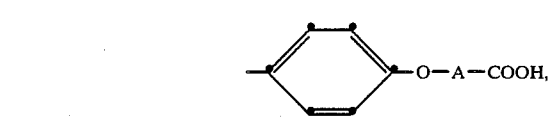

A is $(C_{1-8})$-alkylene, and the salts thereof, wherein said salts are formed from inorganic or organic bases.

2. A compound according to claim 1 which is 4-[10,15,20-tris(4-sulphophenyl)-21H,23H-porphin-5-yl]-benzoic acid.

3. A compound according to claim 1 which is [4-[10,15,20-tris(4-sulphophenyl)-21H-23H-porphin-5-yl]phenoxy]acetic acid.

4. A compound according to claim 1 which is 6-[4-[10,15,20-tris(4-sulphophenyl)-21H,23H-porphin-5-yl]phenyl]hexanecarboxylic acid.

5. A compound according to claim 1 which is 1-(carboxymethyl)-1',1'',1'''-trimethyl-4,4',4'',4'''-(21H,23H-porphin-5,10,15,20-tetrayl)tetrakispyridinium tetraiodide.

6. Compounds of the formula

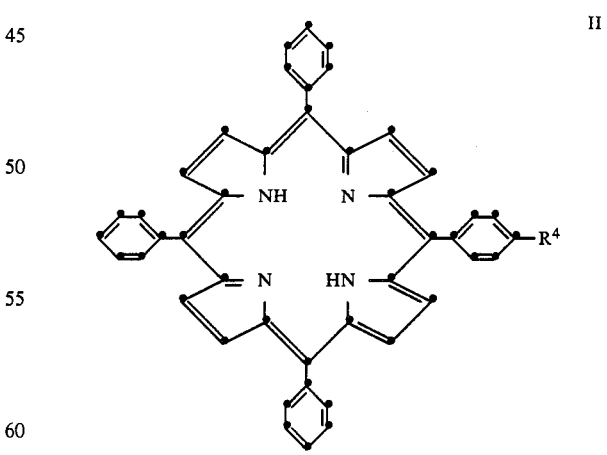

wherein $R^4$ is selected from the group consisting of —COOH, —A—COOH and —O—A—COOH and A is $(C_{1-8})$alkylene.

7. Compounds of the formula

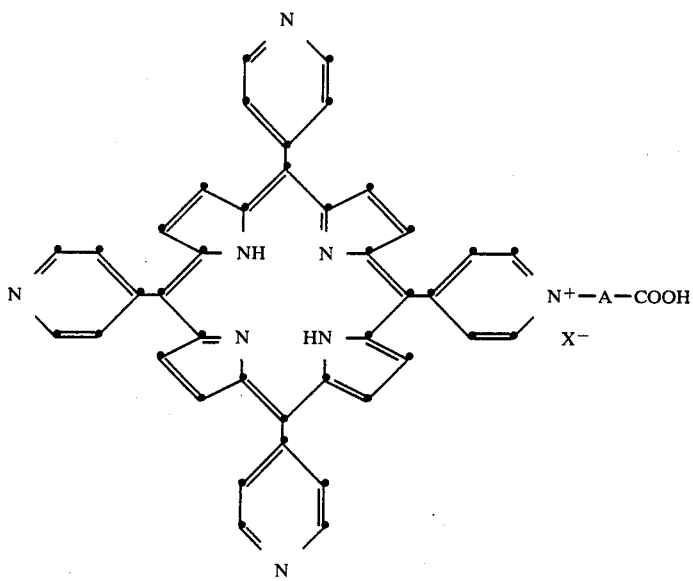

wherein X⁻ is selected from the group consisting of halogen ions, benzenesulfonate ions, p-toluenesulfonate ions, ($C_{1-12}$)-alkylsulfonate ions and ($C_{1-12}$)-alkyl sulphate ions and A is ($C_{1-8}$)-alkylene.

8. A fluorescent antibody, consisting essentially of an antibody specific to an antigen to be detected, and, conjugated to said antibody, a fluorescent compound of the formula

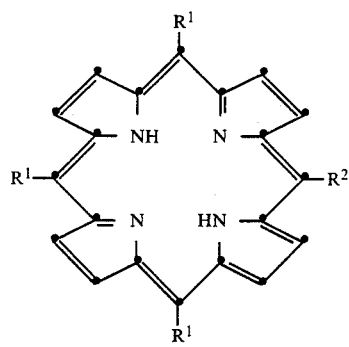

wherein $R^1$ is

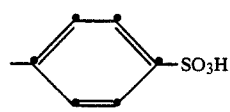

and $R^2$ is

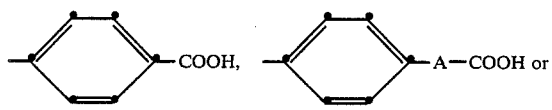

-continued

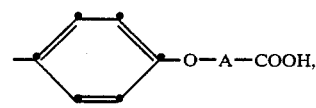

A is ($C_{1-8}$)-alkylene and the salts of said fluorescent compound, wherein said salts are formed from inorganic or organic bases.

9. A fluorescent antibody according to claim 8 wherein the antibody is specific to carcinoembryonal antigen.

10. A fluorescent antibody according to claim 11 wherein a water-soluble carbodiimide derivative couples the antibody to said fluorescent compound.

11. In an immunoassay of the time resolving type which utilizes an antibody conjugated to fluorescent label, the improvement which comprises using as said label a compound of the formula

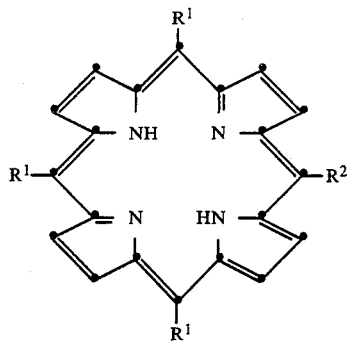

wherein $R^1$ is

and
R² is

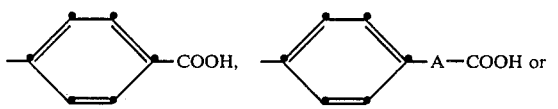

A is (C₁₋₈)-alkylene and the salts thereof wherein said salts are formed from inorganic or organic bases.

12. A porphyrin compound of the formula:

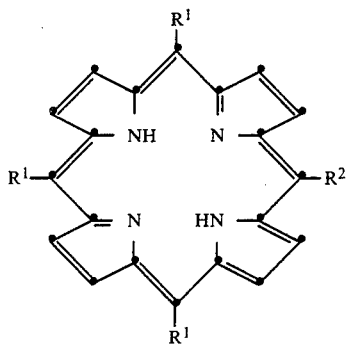

wherein
R¹ is

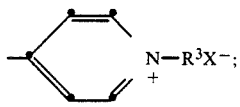

R² is

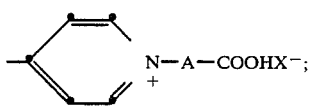

$X^-$ is selected from the group consisting of halogen ions, benzene sulfonate ions, p-toluenesulfonate ions, (C₁₋₁₂)-alkylsulfonate ions and (C₁₋₁₂)-alkyl sulphate ions; A is (C₁₋₈)-alkylene; and R³ is (C₁₋₄)-alkyl.

13. A compound according to claim 12 wherein R¹ is

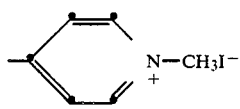

and
R² is

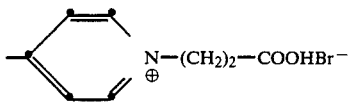

14. A compound according to claim 12 wherein R² is

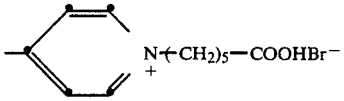

15. A compound according to claim 1 wherein said salts are alkali metal salts or ammonium salts.

16. A compound according to claim 15 wherein said salt is the sodium salt.

17. A compound according to claim 12 wherein $X^-$ is p-toluenesulfonate ion.

18. A compound according to claim 12 wherein $X^-$ is halogen ion.

19. A fluorescent antibody according to claim 10 wherein said carbodiimide derivative is 1-cyclohexyl-3-(2-morpholinoethyl)-carbodiimide methyl-p-toluenesulfonate.

20. A fluorescent antibody consisting essentially of, an antibody specific to an antigen to be detected, and, conjugated to said antibody, a fluorescent compound of the formula

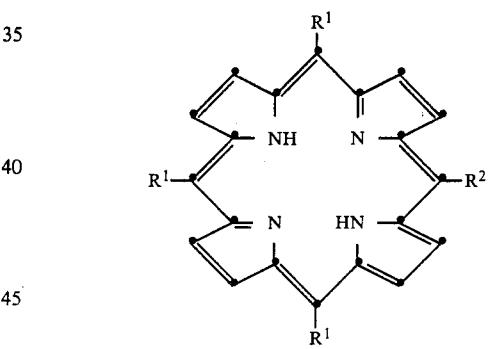

wherein
R¹ is

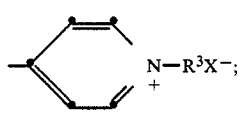

R² is

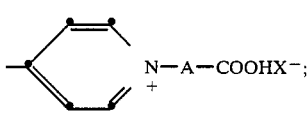

$X^-$ is selected from the group consisting of halogen ions, benzene sulfonate ions, p-toluenesulfonate ions, (C₁₋₁₂)-alkylsulfonate ions and (C₁₋₁₂)-alkyl sulphate ions; R³ is (C₁₋₄)-alkyl.

21. A fluorescent antibody according to claim 20 wherein the antibody is specific to carcinoembryonal antigen.

22. A fluorescent antibody according to claim 21 wherein a water-soluble carbodiimide derivative couples said antibody to said fluorescent compound.

23. A fluorescent antibody according to claim 22 wherein said carbodiimide derivative is 1-cyclohexyl-3-(2-morpholinoethyl)-carbodiimide methyl-p-toluenesulfonate.

24. In an immunoassay of the time resolving type which utilizes an antibody conjugated to fluorescent label, the improvement which comprises using as said label a compound of the formula:

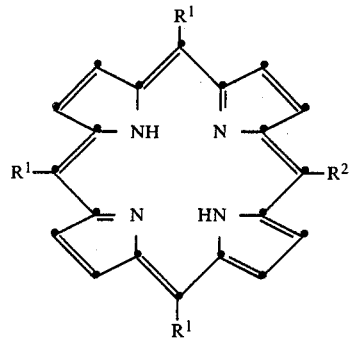

wherein
$R^1$ is

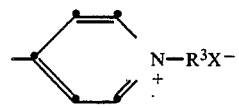

$R^2$ is

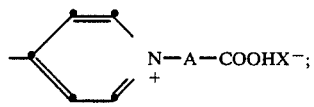

$X^-$ is selected from the group consisting of halogen ions, benzene sulfonate ions, p-toluenesulfonate ions, $(C_{1-12})$-alkylsulfonate ions and $(C_{1-12})$-alkyl sulphate ions; $R^3$ is $(C_{1-4})$-alkyl.

* * * * *